US011471083B2

(12) United States Patent
Lee et al.

(10) Patent No.: US 11,471,083 B2
(45) Date of Patent: Oct. 18, 2022

(54) SYSTEM AND METHOD FOR CAMERA-BASED STRESS DETERMINATION

(71) Applicant: NURALOGIX CORPORATION, Toronto (CA)

(72) Inventors: Kang Lee, Toronto (CA); Pu Zheng, North York (CA); Si Wu, Newmarket (CA)

(73) Assignee: NURALOGIX CORPORATION, Toronto (CA)

( * ) Notice: Subject to any disclaimer, the term of this patent is extended or adjusted under 35 U.S.C. 154(b) by 60 days.

(21) Appl. No.: 16/342,090

(22) PCT Filed: Oct. 24, 2018

(86) PCT No.: PCT/CA2018/051346
§ 371 (c)(1),
(2) Date: Apr. 15, 2019

(87) PCT Pub. No.: WO2019/079896
PCT Pub. Date: May 2, 2019

(65) Prior Publication Data
US 2021/0361208 A1   Nov. 25, 2021

Related U.S. Application Data

(60) Provisional application No. 62/576,384, filed on Oct. 24, 2017.

(51) Int. Cl.
*G06K 9/00* (2022.01)
*A61B 5/16* (2006.01)
(Continued)

(52) U.S. Cl.
CPC ............ *A61B 5/165* (2013.01); *A61B 5/0077* (2013.01); *A61B 5/02405* (2013.01);
(Continued)

(58) Field of Classification Search
CPC ... A61B 5/165; A61B 5/0077; A61B 5/02405; A61B 5/14546; A61B 5/318;
(Continued)

(56) References Cited

U.S. PATENT DOCUMENTS 8,219,438 B1    7/2012  Moon et al.
10,360,443 B2 *  7/2019  Lee ..................... G06V 10/143
(Continued)

FOREIGN PATENT DOCUMENTS

CA    2942852 A1    9/2014
CA    3013948 A1    8/2017
(Continued)

OTHER PUBLICATIONS

International Search Report corresponding to PCT/CA2018/051346; Canadian Intellectual Property Office; dated Feb. 12, 2019.
(Continued)

*Primary Examiner* — Shervin K Nakhjavan
(74) *Attorney, Agent, or Firm* — Bhole IP Law; Anil Bhole; Marc Lampert

(57) ABSTRACT

A system and method for camera-based stress determination. The method includes: determining a plurality of regions-of-interest (ROIs) of a body part; determining a set of bitplanes in a captured image sequence for each ROI that represent HC changes using a trained machine learning model, the machine learning model trained with a hemoglobin concentration (HC) changes training set, the HC changes training set trained using bitplanes from previously captured image sequences of other human individuals as input and received cardiovascular data as targets; determining an HC change signal for each of the ROIs based on changes in the set of determined bitplanes; for each ROI, determining intervals between heartbeats based on peaks in the HC change signal; determining heart rate variability using the intervals between
(Continued)

heartbeats; determining a stress level using at least one determination of a standard deviation of the heart rate variability; and outputting the stress level.

20 Claims, 9 Drawing Sheets

(51) Int. Cl.
| | |
|---|---|
| *G16H 50/20* | (2018.01) |
| *A61B 5/318* | (2021.01) |
| *A61B 5/00* | (2006.01) |
| *A61B 5/024* | (2006.01) |
| *A61B 5/145* | (2006.01) |
| *G06N 3/08* | (2006.01) |

(52) U.S. Cl.
CPC .......... *A61B 5/14546* (2013.01); *A61B 5/318* (2021.01); *A61B 5/7246* (2013.01); *A61B 5/7257* (2013.01); *A61B 5/7267* (2013.01); *G06N 3/08* (2013.01); *G16H 50/20* (2018.01)

(58) Field of Classification Search
CPC ... A61B 5/7246; A61B 5/7257; A61B 5/7267; A61B 5/004; A61B 5/4806; A61B 5/6803; A61B 5/02416; A61B 5/0205; A61B 5/0022; A61B 5/7465; A61B 5/6898; G06N 3/08; G16H 50/20; G16H 80/00; G06T 7/90; G06T 2207/10016; G06T 2207/30201; G06T 2207/30076; G06V 40/161
See application file for complete search history.

(56) References Cited

U.S. PATENT DOCUMENTS

| | | | |
|---|---|---|---|
| 2005/0054935 A1* | 3/2005 | Rice | A61B 5/0059 600/476 |
| 2006/0056509 A1 | 3/2006 | Suino et al. | |
| 2007/0202477 A1 | 8/2007 | Nakagawa | |
| 2008/0235165 A1 | 9/2008 | Movellan et al. | |
| 2009/0318773 A1 | 12/2009 | Jung et al. | |
| 2011/0251493 A1 | 10/2011 | Poh et al. | |
| 2012/0245443 A1 | 9/2012 | Atsumori et al. | |
| 2012/0257035 A1 | 10/2012 | Larsen | |
| 2014/0072190 A1 | 3/2014 | Wu et al. | |
| 2014/0107439 A1 | 4/2014 | Asumori et al. | |
| 2014/0112556 A1 | 4/2014 | Kalinli-Akbacak | |
| 2014/0336479 A1 | 11/2014 | Ando | |
| 2014/0365272 A1 | 12/2014 | Hurewitz | |
| 2015/0190061 A1* | 7/2015 | Godavarty | G01J 3/0272 600/328 |
| 2016/0098592 A1* | 4/2016 | Lee | G06V 30/194 434/236 |
| 2016/0302735 A1* | 10/2016 | Noguchi | A61B 5/02416 |
| 2018/0314879 A1* | 11/2018 | Khwaja | A61B 5/0295 |
| 2020/0252555 A1* | 8/2020 | Choi | H04N 5/23203 |

FOREIGN PATENT DOCUMENTS

| | | |
|---|---|---|
| CA | 3013959 A1 | 8/2017 |
| EP | 2762066 A1 | 8/2014 |
| WO | 2013166341 A1 | 11/2013 |
| WO | 2013190678 A1 | 12/2013 |
| WO | 2014128273 A1 | 8/2014 |
| WO | 2015098977 A1 | 7/2015 |
| WO | 2016049757 A1 | 4/2016 |
| WO | 2016069788 A1 | 5/2016 |
| WO | WO-2017139895 A1 * | 8/2017 ........... A61B 5/0035 |

OTHER PUBLICATIONS

Written Opinion of the International Searching Authority corresponding to PCT/CA2018/051346; Canadian Intellectual Property Office; dated Feb. 12, 2019.

Yanushkevich et al: "Decision-Making Support in Biometric-Based Physical Access Control Systems: Design Concept, Architecture, and Applications" in: "Biometrics", Oct. 26, 2009 (Oct. 26, 2009), pp. 599-631.

Jimenez et al. "A practical appearance model for dynamic facial color", ACM Trans. Graph., 29(6):I41:1-I41:I0, Dec. 2010.

Ramirez et al. "Color Analysis of Facial Skin: Detection of Emotional State", 2014 IEEE Conference on Computer Vision and Pattern Recognition Workshops, Jun. 23-28, 2014 (Jun. 28, 2014), pp. 474-479.

Wioleta, "Using Physiological Signals for Emotion Recognition", The 6th International Conference on Human System Interaction (HSI), Sopot, Poland, Jun. 6-8, 2013, pp. 556-561.

Nguyen et al. "Investigating Brain Activity When Listening to Different Types of Music by Near-Infrared Spectroscopy", 29th Southern Biomedical Engineering Conference, 2013, pp. 83-86.

International Search Report corresponding to PCT/CA2017/050140 dated May 15, 2017.

Written Opinion corresponding to PCT/CA2017/050140 dated May 15, 2017.

Tsumura et al, "Image-based skin color and texture analysis/ synthesis by extracting hemoglobin and melanin information in the skin", Proc. ACM Transactions on Graphics, SIGGRAPH 2003.

Alkawaz et al (Mar. 31, 2015): The Correlation Between Blood Oxygenation Effects and Human Emotion Towards Facial Skin Colour ofVirtual Human 3D Research. Vol.6 (2). pp. I-16.

McDuff et al (Aug. 2014): Remote Measurement of Cognitive Stress via Heart Rate Variability. IEEE Engineering in Medicine and Biology Society 2014 pp. 2957-2960.

Antink et al (Jul. 15, 2015): Beat-to-Beat Heart Rate Estimation Fusing Multimodal Video and Sensor Data. 2015 Optical Society of America. vol. 6 (8). pp.2895-2907.

Yoo et al (Jun. 17, 2011): Mental Stress Assessment Based on Pulse Photoplethysmography. IEEE 15' International Symposium on Consumer Electronics, pp. 323-326.

Bogdan et al (May 2015): Remote Assessment of Heart Rate by Skin Color Processing. 2015 IEEE International Black Sea Conference on Communications and Networking, pp. I12-116.

International Search Report corresponding to PCT/CA2017/050207 dated May 31, 2017.

Written Opinion corresponding to PCT/CA2017/050207 dated May 31, 2017.

Yong et al., "Colour Perception on Facial Expression towards Emotion", Telkomnika, vol. 10, No. 4, Dec. 2012 (Dec. 2012), pp. 783-794, ISSN:1693-6930.

Alkawaz et al., "A Crucial Investigation of Facial Skin Colour Research Trend and Direction", International Journal of Multimedia and Ubiquitous Engineering, vol. 10, No. 1, Jan. 2015 (Jan. 2015), pp. 295-316, ISSN:1975-0080 IJMUE http://dx.doi.org/10.14257/ijmue.2015.10.1.29.

International Search Report corresponding to PCT/CA2015/050975 dated Nov. 20, 2015.

Written Opinion corresponding to PCT/CA2015/050975 dated Nov. 20, 2015.

Office Action corresponding to U.S. Appl. No. 14/868,601; United States Patent and Trademark Office dated Oct. 19, 2017.

Poh (NPL, Advancements in Noncontact, Multiparameter Physiological Measurements Using a Webcam.

Office Action corresponding to U.S. Appl. No. 14/868,601; United States Patent and Trademark Office dated May 14, 2018.

Office Action corresponding to U.S. Appl. No. 14/868,601; United States Patent and Trademark Office dated Nov. 2, 2018.

Office Action corresponding to U.S. Appl. No. 14/868,601; United States Patent and Trademark Office dated Apr. 11, 2019.

\* cited by examiner

US 11,471,083 B2

SYSTEM AND METHOD FOR CAMERA-BASED STRESS DETERMINATION

TECHNICAL FIELD

The following relates generally to detection of human stress and more specifically to a system and method for camera-based stress determination.

BACKGROUND

Humans often and regularly encounter various stressful situations. Such stress, when experienced at a high degree and/or for a long duration of time, can lead to a myriad of deleterious health consequences; for example, cardiovascular diseases, cognitive dysfunctions, and psychological disorders. Generally, assessment of stress relies on the use of self-report questionnaires or physiological instruments, such as an electrocardiogram (ECG). While self-report questionnaires can provide a glimpse into a person's psychological state and stress level, the results from such questionnaires are generally considered to be highly unreliable given the susceptibility to response bias. Physiological measurements, such as those received from an ECG, can be reliably used to measure stress. However, physiological instruments are generally invasive and generally require a trained professional to operate. As an example, use of an ECG requires the attachment of electrodes onto the subject's body by trained individuals, which is generally not only highly invasive but also inconvenient. Thus, other approaches to measuring stress are, for example, either unreliable, inconvenient, or both.

SUMMARY

In an aspect, there is provided a method for camera-based stress determination of a human individual, the method comprising: receiving an image sequence capturing a body part of the human individual; determining a plurality of regions-of-interest (ROIs) of the body part based on features of the body part; determining a set of bitplanes in the captured image sequence for each ROI that represent HC changes of the human individual using a trained machine learning model, the machine learning model trained with a hemoglobin concentration (HC) changes training set, the HC changes training set trained using bitplanes from previously captured image sequences of other human individuals as input and received cardiovascular data as targets; determining an HC change signal for each of the ROIs based on changes in the set of determined bitplanes; for each ROI, determining intervals between heartbeats based on peaks in the HC change signal; determining heart rate variability using the intervals between heartbeats; determining a stress level using at least one determination of a standard deviation of the heart rate variability; and outputting the stress level.

In a particular case, the cardiovascular data comprises hemodynamic changes measured by an electrocardiograph.

In another case, the bitplanes are in a red channel, green channel, and blue channel of each image of the image sequence.

In yet another case, the machine learning model comprises a Long Short Term Memory (LSTM) neural network.

In yet another case, the output of the LSTM neural network comprises a matrix of bitplane composition weights as the determined set of bitplanes.

In yet another case, the body part is the individual's face.

In yet another case, determining a plurality of ROIs comprises tracking the human individual's face in each frame of the captured image sequence to track the ROIs.

In yet another case, determining intervals between heartbeats comprises: applying fast Fourier transform (FFT) and band pass filtering to determine a principle frequency component; using the principle frequency component, reconstructing peaks of each heartbeat; and determining intervals between the reconstructed peaks.

In yet another case, determining heart rate variability comprises generating a Poincare plot of the heartbeat intervals.

In yet another case, determining the stress level comprises: determining a first standard deviation of points of heart rate variability in a direction perpendicular to a line of identity of the Poincare plot; determining a first standard deviation of points of heart rate variability in a direction that is along the line of identity; determining a measure of stress as a correlation to the second standard divided by the first standard deviation.

In yet another case, determining the measure of stress further comprises performing a Fisher z-transformation to the second standard divided by the first standard deviation.

In another aspect, there is provided a system for camera-based stress determination of a human individual, the system comprising at least one processing unit and a data storage, the at least one processing unit in communication with the data storage and configured to execute: a transdermal optical imaging (TOI) module to receive an image sequence capturing a body part of the human individual, and to determine a plurality of regions-of-interest (ROIs) of the body part based on features of the body part; a data science module to determine a set of bitplanes in the captured image sequence for each ROI that represent HC changes of the human individual using a trained machine learning model, the machine learning model trained with a hemoglobin concentration (HC) changes training set, the HC changes training set comprising bitplanes from previously captured image sequences of other human individuals as input and received cardiovascular data as targets, the TOI module determining an HC change signal for each of the ROIs based on changes in the set of determined bitplanes; a reconstruction module to determine intervals between heartbeats based on peaks in the HC change signal; a stress module to determine heart rate variability using the intervals between heartbeats, and to determine a stress level using at least one determination of a standard deviation of the heart rate variability; and an output module to output the stress level.

In a particular case, the cardiovascular data comprises hemodynamic changes received from an electrocardiograph.

In another case, the bitplanes are in a red channel, green channel, and blue channel of each image of the image sequence.

In yet another case, the body part is the individual's face.

In yet another case, determining a plurality of ROIs comprises tracking the human individual's face in each frame of the captured image sequence to track the ROIs.

In yet another case, the reconstruction module determines intervals between heartbeats by: applying fast Fourier transform (FFT) and band pass filtering to determine a principle frequency component; using the principle frequency component, reconstructing peaks of each heartbeat; and determining intervals between the reconstructed peaks.

In yet another case, the stress module determines heart rate variability by generating a Poincare plot of the heartbeat intervals.

In yet another case, the stress module determines the stress level by: determining a first standard deviation of points of heart rate variability in a direction perpendicular to a line of identity of the Poincare plot; determining a first standard deviation of points of heart rate variability in a direction that is along the line of identity; determining a measure of stress as a correlation to the second standard divided by the first standard deviation.

In yet another case, the stress module determines the measure of stress by performing a Fisher z-transformation to the second standard divided by the first standard deviation.

These and other aspects are contemplated and described herein. It will be appreciated that the foregoing summary sets out representative aspects of systems and methods to assist skilled readers in understanding the following detailed description.

BRIEF DESCRIPTION OF THE DRAWINGS

The features of the invention will become more apparent in the following detailed description in which reference is made to the appended drawings wherein.

DETAILED DESCRIPTION

Figure 1:
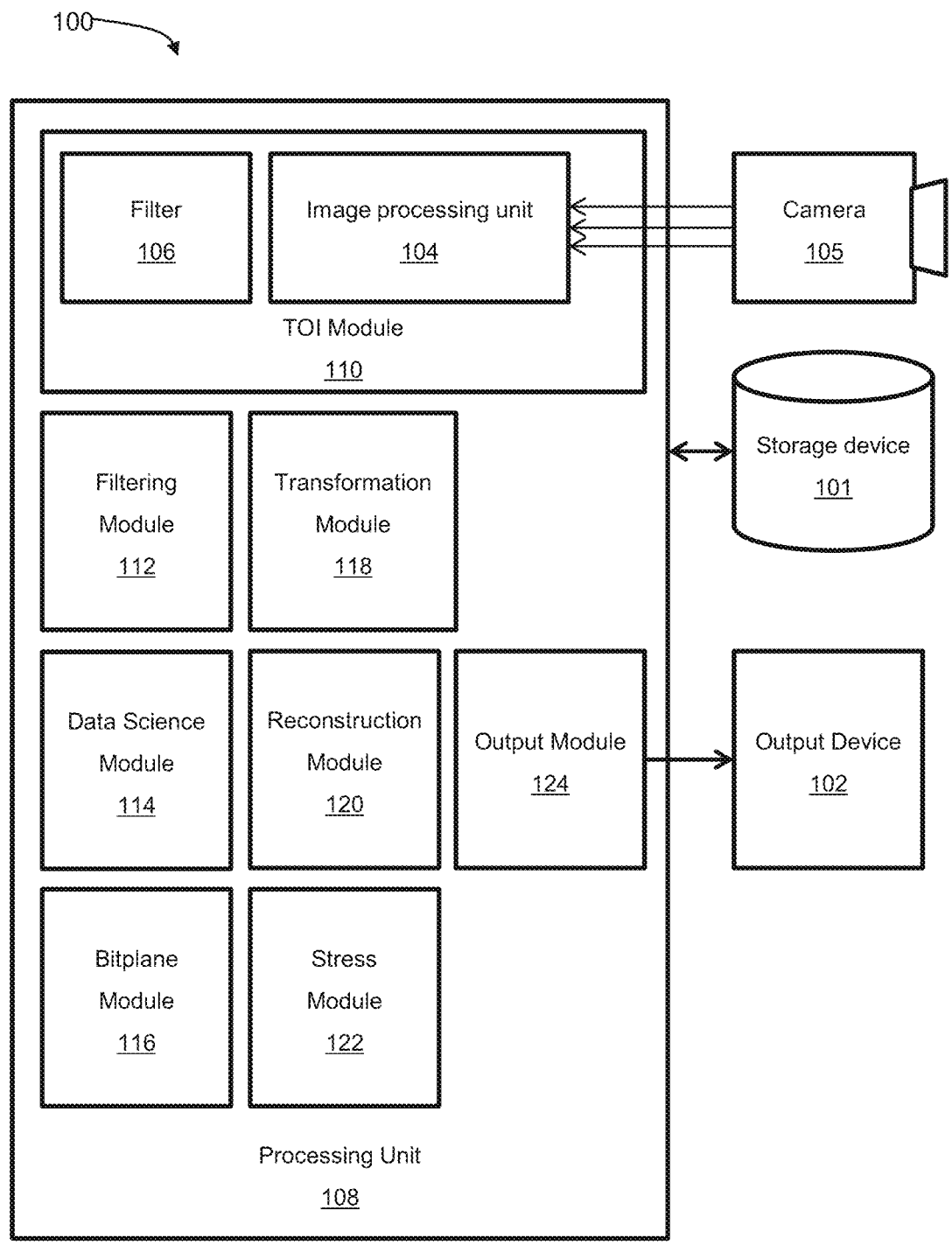
FIG. 1 is a block diagram of a system for camera-based heart rate tracking, according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to detection of human stress and more specifically to a system and method for camera-based stress determination.

It has been determined that an individual's stress can be observed by measuring heart rate variability including respiratory sinus arrhythmia. Given a stressful situation where an individual encounters a perceived threat, the autonomic nervous system generally works to adjust the internal state of the individual's body and react to the situation. The two branches of the autonomic nervous system, the sympathetic and parasympathetic nervous systems, contribute in stress reaction. The sympathetic nervous system is generally concerned with challenges from the external environment, for example triggering the fight-or-flight response in stressful situations. The parasympathetic nervous system is generally concerned with returning the body to a resting state or the state of homeostasis. It has been determined that stress generally occurs when the parasympathetic nervous system fails to maintain homeostasis. Thus, a determination of stress can be obtained by examining the level of homeostasis.

As part of the parasympathetic nervous system, the vagus nerve generally plays a large role in the regulation of homeostasis because it is responsible for signaling the heart, lungs, and digestive tract to slow down and relax. The activity of the vagus nerve, otherwise known as vagal tone, can thus be indicative of the level of homeostasis within the body. Generally, with increased vagal tone, the heart slows down, homeostasis is maintained, and stress level decreases. Generally, with decreased vagal tone, the heart quickens, homeostasis is disrupted, and stress level increases. It has been shown that parasympathetic vagal activity, as measured by an electrocardiogram (ECG), decreases during sessions involving stress. In addition, it has been shown that irregular increase and decrease of vagal tone can indicate chronic stress.

Although vagal tone can provide insight into an individual's stress level, the changes in vagal tone generally cannot be measured directly. Rather, it has been found that vagal tone, and corresponding information involving stress, can be measured indirectly but reliably by one or more heart rate variability indices, for example respiratory sinus arrhythmia (RSA). RSA is the rhythmic increase and decrease in the beating of the heart, which occurs in the presence of breathing. Typically, heart rate increases with inhalation and decreases with exhalation. It has been shown that a decrease in resting RSA is indicative of increased stress.

As part of an approach to measuring RSA, a measurement of variations in heartbeat can be first obtained. In a particular approach, ECG can be used to observe heart rate variability (HRV), analyzing the time-period in milliseconds between each R-wave, to obtain an R-R interval (RRI). With information from the RRI, reliable inferences can be made about stress. An increasing RRI variation can indicate excitation of the vagus nerve as it works to decrease heart rate, and thus can indicate that stress level is low. A decreasing RRI variation can indicate an inhibited vagus nerve, allowing heart rate to increase, and thus can indicate that stress level is high. However, assessment of RRI may not be enough to determine vagal tone because respiration is typically not the only contributor to variations in heart rate. As an example, there may be oscillations at frequencies slower than that of respiration, such as Traube-Hering-Mayer waves; which can provide information regarding the sympathetic nervous system rather than the parasympathetic nervous system. Thus, data from ECG recordings typically has to be filtered to obtain various hear rate variability (HRV) features, including measurement of RSA, and in effect can be an estimate of vagal tone that can provide information regarding individual stress level.

Use of an ECG can be effective and reliable at assessing individual stress level; however, there are generally limitations with its utilization. ECG is generally expensive, invasive, and inconvenient. First, ECG is typically expensive because it requires the utilization of specialized equipment (for example, ECG electrodes, leads, and machine). In addition, the interpretation of electrocardiographs typically requires specially trained medical professionals, whose time and expertise can be expensive. Second, ECG is typically invasive because its utilization of electrodes requires attachment of said electrodes to the human body, which can cause discomfort. Third, ECG is typically inconvenient because the application of electrodes typically necessitates the preparation of the skin surface to reduce skin impedance in order to obtain a clean ECG signal. The combination of these limitations means that ECG is particularly inconvenient because it cannot be used in all settings. In many cases, these limitations are problematic for the assessment of stress because individuals commonly experience stress at various times in their day, such as at work, home, or school. Yet, with ECG, individuals are typically limited to assessments of their stress during occasional and cumbersome visits to a medical facility with an ECG device in order to determine whether their stress level has reached an unhealthy state.

Referring now to FIG. 1, a system for camera-based heart rate tracking 100 is shown. The system 100 includes a processing unit 108, one or more video-cameras 100, a storage device 101, and an output device 102. The processing unit 108 may be communicatively linked to the storage device 101, which may be preloaded and/or periodically loaded with video imaging data obtained from one or more video-cameras 100. The processing unit 108 includes various interconnected elements and modules, including a transdermal optical imaging (TOI) module 110, a filtering module 112, a data science module 114, a bitplane module 116, a transformation module 118, a reconstruction module 120, a stress module 122, and an output module 124. In a particular case, the TOI module includes an image processing unit 104 and a filter 106. The video images captured by the video-camera 105 can be processed by the filter 106 and stored on the storage device 101. In further embodiments, one or more of the modules can be executed on separate processing units or devices, including the video-camera 105 or output device 102. In further embodiments, some of the features of the modules may be combined or run on other modules as required.

The term "video", as used herein, can include sets of still images. Thus, "video camera" can include a camera that captures a sequence of still images.

Figure 3:
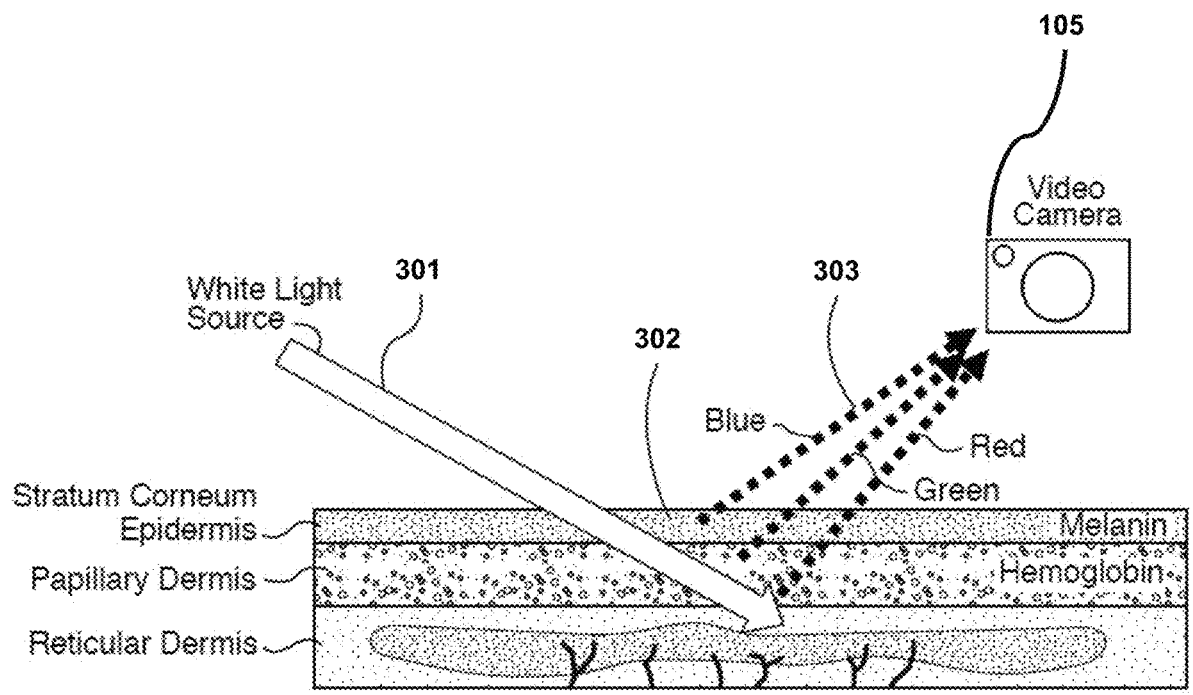
FIG. 3 is an illustration of re-emission of light from skin epidermal and subdermal layers.
Figure 4:
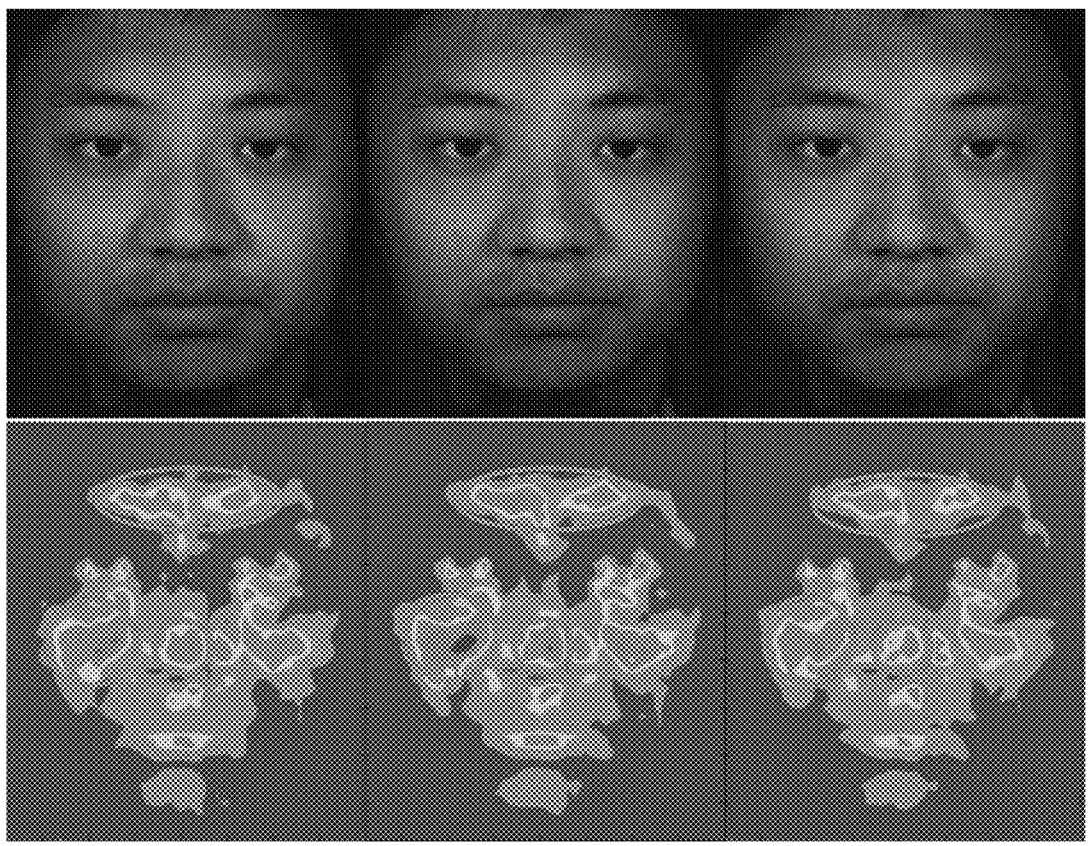
FIG. 4 is a set of surface and corresponding transdermal images illustrating change in hemoglobin concentration for a particular human subject at a particular point in time.

Using transdermal optical imaging (TOI), the TOI module 110 can isolate hemoglobin concentration (HC) from raw images taken from a traditional digital camera. Referring now to FIG. 3, a diagram illustrating the re-emission of light from skin is shown. Light 301 travels beneath the skin 302, and re-emits 303 after travelling through different skin tissues. The re-emitted light 303 may then be captured by optical cameras 100. The dominant chromophores affecting the re-emitted light are melanin and hemoglobin. Since melanin and hemoglobin have different color signatures, it has been found that it is possible to obtain images mainly reflecting HC under the epidermis as shown in FIG. 4.

Using transdermal optical imaging (TOI), the TOI module 110, via the image processing unit 104, obtains each captured image or video stream, from the camera 105, and performs operations upon the image to generate a corresponding optimized hemoglobin concentration (HC) image of the subject. From the HC data, the HC can be determined. The image processing unit 104 isolates HC in the captured video sequence. In an exemplary embodiment, the images of the subject's faces are taken at 30 frames per second using a digital camera 105. It will be appreciated that this process may be performed with alternative digital cameras, lighting conditions, and frame rates.

In a particular case, isolating HC can be accomplished by analyzing bitplanes in the sequence of video images to determine and isolate a set of the bitplanes that approximately maximize signal to noise ratio (SNR). The determination of high SNR bitplanes is made with reference to a first training set of images constituting the captured video sequence, in conjunction with blood pressure wave data gathered from the human subjects. In some cases, this data is supplied along with other devices, for example, ECG, pneumatic respiration, continuous blood pressure, laser Doppler data, or the like, collected from the human subjects, and received, in order to provide ground truth blood flow data to train the training set for HC change determination. A blood flow training data set can consist of blood pressure wave data obtained from human subjects by using one or more continuous blood pressure measurement devices as ground truth data; for example, an intra-arterial blood pressure measurement approach, an auscultatory approach, or an oscillometric approach. The selection of the training data set based on one of these three exemplary approaches depends on a setting in which the continuous blood pressure measurement system is used; as an example, if the human subject is in a hospital intensive care setting, the training data can be received from an intra-arterial blood pressure measurement approach.

Figure 8:
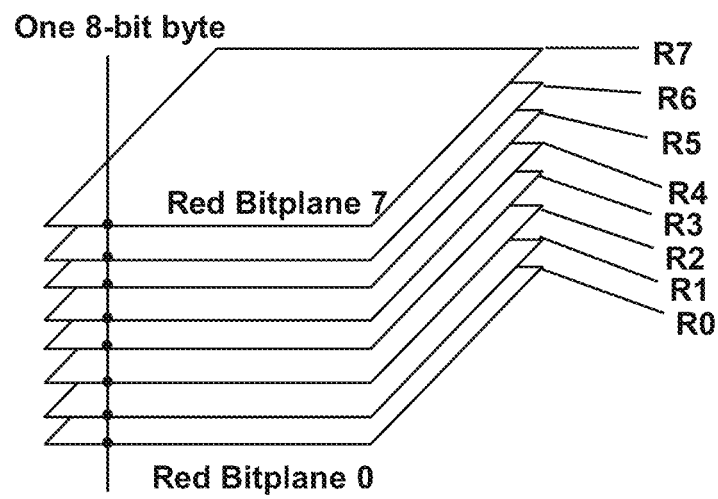
FIG. 8 is an illustration of bitplanes for a three channel image.
Figure 8:
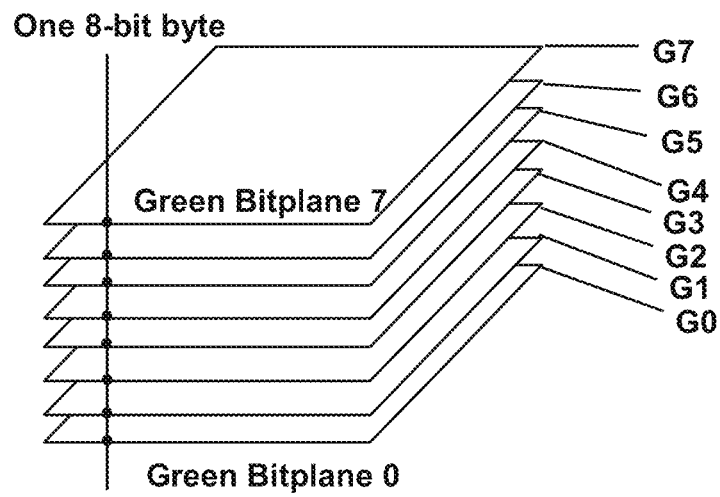
Figure 8:
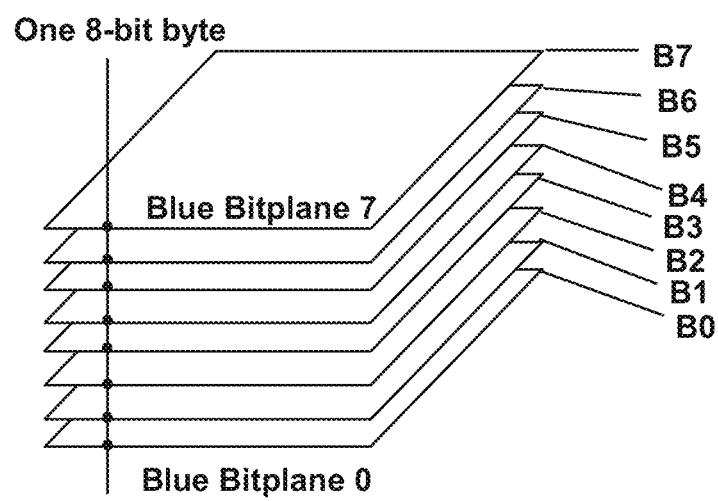

Bitplanes are a fundamental aspect of digital images. Typically, a digital image consists of certain number of pixels (for example, a width X height of 1920×1080 pixels). Each pixel of the digital image having one or more channels (for example, color channels red, green, and blue (RGB)). Each channel having a dynamic range, typically 8 bits per pixel per channel, but occasionally 10 bits per pixel per channel for high dynamic range images. Whereby, an array of such bits makes up what is known as the bitplane. In an example, for each image of color videos, there can be three channels (for example, red, green, and blue (RGB)) with 8 bits per channel. Thus, for each pixel of a color image, there are typically 24 layers with 1 bit per layer. A bitplane in such a case is a view of a single 1-bit map of a particular layer of the image across all pixels. For this type of color image, there are therefore typically 24 bitplanes (i.e., a 1-bit image per plane). Hence, for a 1-second color video with 30 frames per second, there are at least 720 (30×24) bitplanes. FIG. 8 is an exemplary illustration of bitplanes for a three-channel image (an image having red, green and blue (RGB) channels). Each stack of layers is multiplied for each channel of the image; for example, as illustrated, there is a stack of bitplanes for each channel in an RGB image. In the embodiments described herein, Applicant recognized the advantages of using bit values for the bitplanes rather than using, for example, merely the averaged values for each channel. Thus, a greater level of accuracy can be achieved for making predictions of HC changes, and thus continuous blood pressure measurements as disclosed herein, and as described for making predictions. Particularly, a greater accuracy is possible because employing bitplanes provides a greater data basis for training the machine learning model.

TOI signals can be taken from regions of interest (ROIs) of the human subject, for example forehead, nose, and cheeks, and can be defined manually or automatically for the video images. The ROIs are preferably non-overlapping. These ROIs are preferably selected on the basis of which HC is particularly indicative of blood pressure measurement. Using the native images that consist of all bitplanes of all three R, G, B channels, signals that change over a particular time period (for example, 10 seconds) on each of the ROIs are extracted.

The raw signals can be pre-processed using one or more filters, depending on the signal characteristics. Such filters may include, for example, a Butterworth filter, a Chebyshev filter, or the like. Using the filtered signals from two or more ROIs, machine learning is employed to systematically identify bitplanes that will significantly increase the signal differentiation (for example, where the SNR improvement is greater than 0.1 db) and bitplanes that will contribute nothing or decrease the signal differentiation. After discarding the latter, the remaining bitplane images can optimally determine HC and HC changes.

With respect to bitplanes, a digital image consists of a certain number of pixels; typically referred to as a configuration of width-times-height (for example, 1920W×1080H). Each pixel has one or more channels associated with it. Each channel has a dynamic range, typically 8 bits per pixel per channel, but occasionally 10 bits per pixel per channel for high dynamic range images. For color videos, each image typically has three channels; for example, Red, Green, and Blue (RGB). In a particular case, there are 8-bits per channel. In some cases, additional channels may be available, such as thermal and depth. As such, a bitplane is a view of a single bit of an image across all pixels; i.e., a 1-bit image per bit per channel.

Machine learning approaches (for example, a Long Short Term Memory (LSTM) neural network, or a suitable alternative such as non-linear Support Vector Machine) and deep learning may be used to assess the existence of common spatial-temporal patterns of hemoglobin changes across subjects. The machine learning process involves manipulating the bitplane vectors (for example, 24 bitplanes X 30 fps) using the bit value in each pixel of each bitplane along the temporal dimension. In one embodiment, this process requires subtraction and addition of each bitplane to maximize the signal differences in all ROIs over the time period. In some cases, to obtain reliable and robust computational models, the entire dataset can be divided into three sets: the training set (for example, 80% of the whole subject data), the test set (for example, 10% of the whole subject data), and the external validation set (for example, 10% of the whole subject data). The time period can vary depending on the length of the raw data (for example, 15 seconds, 60 seconds, or 120 seconds). The addition or subtraction can be performed in a pixel-wise manner. A machine learning approach, the Long Short Term Memory (LSTM) neural network, or a suitable alternative thereto is used to efficiently and obtain information about the improvement of differentiation in terms of accuracy, which bitplane(s) contributes the best information, and which does not in terms of feature selection. The Long Short Term Memory (LSTM) neural network allow us to perform group feature selections and classifications. The LSTM machine learning algorithm are discussed in more detail below. From this process, the set of bitplanes to be isolated from image sequences to reflect temporal changes in HC is obtained for determination of blood pressure.

To extract facial blood flow data, facial HC change data on each pixel or ROI of each subject's body part image is extracted as a function of time when the subject is being viewed by the camera 103. In some cases, to increase signal-to-noise ratio (SNR), the subject's body part can be divided into the plurality of regions of interest (ROIs). The division can be according to, for example, the subject's differential underlying physiology, such as by the autonomic nervous system (ANS) regulatory mechanisms. In this way, data in each ROI can be averaged. The ROIs can be manually selected or automatically detected with the use of a face tracking software. The machine learning module 112 can then average the data in each ROI. This information can then form the basis for the training set. As an example, the system 100 can monitor stationary HC changes contained by a selected ROI over time, by observing (or graphing) the resulting temporal profile (for example, shape) of the selected ROI HC intensity values over time. In some cases, the system 100 can monitor more complex migrating HC changes across multiple ROIs by observing (or graphing) the spatial dispersion (HC distribution between ROIs) as it evolves over time.

A Long Short Term Memory (LSTM) neural network, or a suitable alternative thereto, can be used to efficiently obtain information about the improvement of differentiation in terms of accuracy, which bitplane(s) contributes the best information, and which does not in terms of feature selection. The Long Short Term Memory (LSTM) neural network allows the system 100 to perform group feature selections and classifications. The LSTM machine learning algorithm is discussed in more detail below. From this process, the set of bitplanes to be isolated from image sequences to reflect temporal changes in HC is obtained. An image filter is configured to isolate the identified bitplanes in subsequent steps described below.

To extract facial blood flow data, HC change data on each pixel of each subject's face image is extracted as a function of time when the subject is being viewed by the camera 105. In some other cases, to increase signal-to-noise ratio (SNR) and reduce demand on computational resources, the system 100 can also use a region of interest approach. In this approach, the system 100 defines regions of interest on the image, and for each bitplane, sums the bit values of all pixels in each region and divides the sum by the number of pixels in that region. This gives the average bit value for each ROI in each bitplane. The subject's face can be divided into a plurality of regions of interest (ROIs) according to, for example, their anatomy or differential underlying physiology.

Machine learning approaches, including deep learning algorithms, (such as a Long Short Term Memory (LSTM) neural network or a suitable alternative such as non-linear Support Vector Machine) may be used to assess the existence of common spatial-temporal patterns of hemoglobin changes across subjects. The Long Short Term Memory (LSTM) neural network or an alternative is trained on the transdermal data from a portion of the subjects (e.g., 70%, 80%, 90%) to obtain a multi-dimensional computational model for the facial blood flow. The models are then tested on the data from the remaining training subjects.

Thus, it is possible to obtain a video sequence of any subject and apply the HC extracted from selected bitplanes to the computational models to determine blood flow waves. For long running video streams with changes in blood flow and intensity fluctuations, changes of the estimation and intensity scores over time relying on HC data based on a moving time window (e.g., 10 seconds) may be reported.

Figure 5:
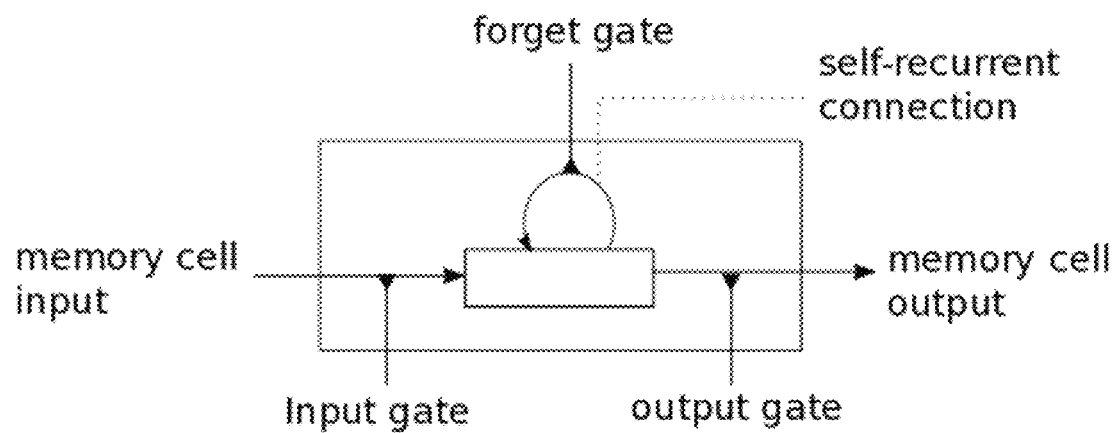
FIG. 5 is a diagrammatic representation of a memory cell.

In an example using the Long Short Term Memory (LSTM) neural network, the LSTM neural network comprises at least three layers of cells. The first layer is an input layer, which accepts the input data. The second (and perhaps additional) layer is a hidden layer, which is composed of memory cells (see FIG. 5). The final layer is an output layer, which generates the output value based on the hidden layer using Logistic Regression.

Each memory cell, as illustrated, comprises four main elements: an input gate, a neuron with a self-recurrent connection (a connection to itself), a forget gate and an output gate. The self-recurrent connection has a weight of 1.0 and ensures that, barring any outside interference, the state of a memory cell can remain constant from one time step to another. The gates serve to modulate the interactions between the memory cell itself and its environment. The input gate permits or prevents an incoming signal to alter the state of the memory cell. On the other hand, the output gate can permit or prevent the state of the memory cell to have an effect on other neurons. Finally, the forget gate can modulate the memory cell's self-recurrent connection, permitting the cell to remember or forget its previous state, as needed.

The equations below describe how a layer of memory cells is updated at every time step t. In these equations: $x_t$ is the input array to the memory cell layer at time t. In our application, this is the blood flow signal at all ROIs $$\vec{x}_t = [x_{1t}, x_{2t}, \ldots, x_{nt}]$$

$W_i$, $W_f$, $W_c$, $W_o$, $U_i$, $U_f$, $U_c$, $U_o$ and $V_o$ are weight matrices; and $b_i$, $b_f$, $b_c$ and $b_o$ are bias vectors First, we compute the values for $i_t$, the input gate, and $\tilde{C}_t$ the candidate value for the states of the memory cells at time t:

$$i_t = \sigma(W_i x_t + U_i h_{t-1} + b_i)$$

$$\tilde{C}_t = \tanh(W_c x_t + U_c h_{t-1} + b_c)$$

Second, we compute the value for $f_t$, the activation of the memory cells' forget gates at time t:

$$f_t = \sigma(W_f x_t + U_f h_{t-1} d + b_f)$$

Given the value of the input gate activation $i_t$, the forget gate activation $f_t$ and the candidate state value $\tilde{C}_t$, we can compute $C_t$, the memory cells' new state, at time t:

$$C_t = i_t * \tilde{C}_t + f_t * C_{t-1}$$

With the new state of the memory cells, we can compute the value of their output gates and, subsequently, their outputs:

$$o_t = \sigma(W_o x_t + U_o h_{t-1} + V_o C_t + b_o)$$

$$h_t = o_t * \tanh(C_t)$$

Based on the model of memory cells, for the blood flow distribution at each time step, we can calculate the output from memory cells. Thus, from an input sequence $x_0, x_1, x_2, \ldots, x_n$, the memory cells in the LSTM layer will produce a representation sequence $h_0, h_1, h_2, \ldots, h_n$.

The goal is to classify the sequence into different conditions. The Logistic Regression output layer generates the probability of each condition based on the representation sequence from the LSTM hidden layer. The vector of the probabilities at time step t can be calculated by:

$$p_t = \text{softmax}(W_{output} h_t + b_{output})$$

where $W_{output}$ is the weight matrix from the hidden layer to the output layer, and $b_{output}$ is the bias vector of the output layer. The condition with the maximum accumulated probability will be the predicted condition of this sequence.

The heart rate tracking approach, used by the system 100 on the HC change data from the TOI module 110, utilizes adaptive weighting of pixels or multiple regions-of-interest (ROIs), and uses minimizing 'noise' criteria to control the weights. The heart rate tracking approach also utilizes a Hilbert transform to extract a coherent signal for the heartbeat. Advantageously, the accuracy when measured against 'ground truth' electrocardiogram (ECG) data indicates that the estimated "beats-per-minute" (BPM) of the heartbeat recovery approach is typically consistent within +/−2 BPM of the ECG data.

The HC data captured by the TOI module 110, as described herein, of a human subject's face, as either 'live' or previously recorded, is used as the source data for determining the subject's heart rate. The facial blood flow data can then be used for estimation of related parameters such as the average heart rate in BPM.

In order to estimate the BPM of the human subject, the TOI module 110 detects, recovers and tracks the valid occurrences of the subject's heartbeat. The system 100 through its various modules, as described herein, then converts these periodic occurrences into an instantaneous statistic representing the average count as BPM. This instantaneous statistic is then continuously updated. Advantageously, this approach has data-sampling that is equal to the video acquisition frame-rate specified as "frames-per-second" (FPS). This provides a continuous per-frame estimation of the instantaneous heart rate.

Advantageously, the embodiments described herein can employ the hemoglobin activity captured by the TOI module 110 to gather information regarding, for example, an individual's heart rate, RRI, and stress level from determining facial hemoglobin activity that is at least partially controlled by the autonomic nervous system (ANS). As ANS can be involved in responding to stress, certain regions of the individual's face can reflect these responses. In a particular case, the sympathetic branch of ANS controls facial blood flow of the eyelids, cheeks, and chin. The parasympathetic branch controls facial blood flow of the nose and ears. In some embodiments, given that the parasympathetic branch has been determined to play a role in maintaining homeostasis, and thus can be responsible for changes in stress level, particular attention can be paid to hemoglobin activities in the nose and ears of an individual.

In the embodiments described herein, TOI images of hemoglobin activity can be used to determine heart rate and RRI. This information can be plotted, such as on a Poincaré scatter plot, and analyzed to determine stress level. Advantageously, the present inventors have determined that TOI can be used to obtain accurate measures of individual stress level based on facial blood flow information.

Figure 2:
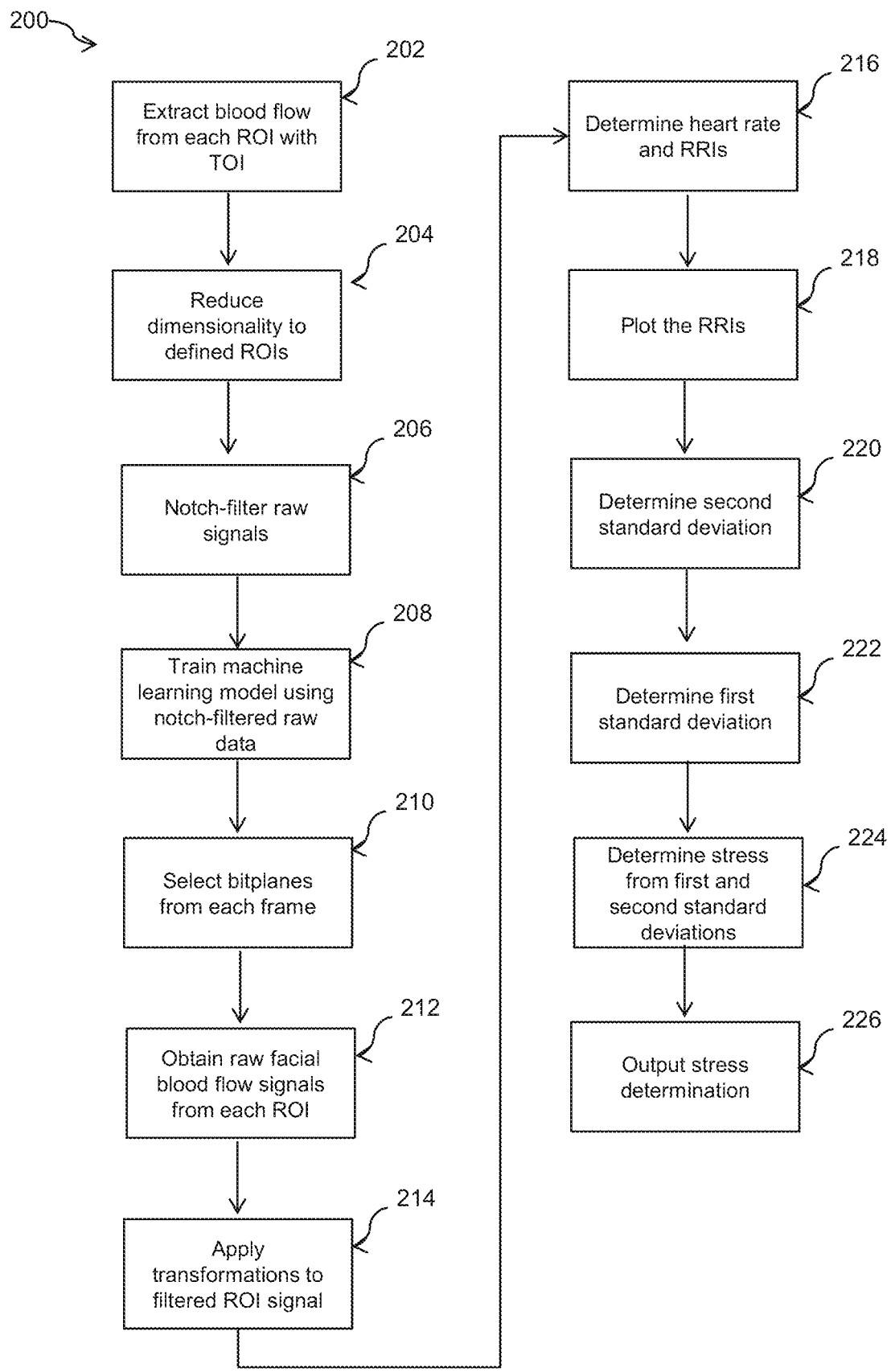
FIG. 2 is a flowchart for a method for camera-based heart rate tracking, according to an embodiment.

Turning to FIG. 2, a flowchart for a method for camera-based stress determination 200 is shown.

At block 202, blood flow information is extracted from a video captured by the camera 105 using transdermal optical imaging of a human individual by the TOI module 110, as described herein, for HC at defined regions-of-interest (ROI). In a particular case, the ROIs are located on the individual's face. In addition, the TOI module 110 records dynamic changes of such HC over time.

For each video, the TOI module 110 determines heart rate based on blood flow information extracted through the transdermal optical imaging (TOI) approach described herein. Melanin and hemoglobin are typically the primary chromophores that influence light-tissue interaction in the visible spectrum, approximately 400-700 nm. It has been determined that absorbance of hemoglobin, whether oxygenated or deoxygenated, generally decreases sharply in the red spectral region (approximately >590-600 nm). It has also been determined that absorbance of melanin generally follows a monotonic decrease in absorption with increased wavelength. This characteristic difference in absorption between hemoglobin and melanin permits the TOI module 110 to separate images reflecting skin hemoglobin concentration from those reflecting skin melanin concentration.

The camera 105 captures images in multiple bitplanes in the Red, Green, and Blue (RGB) channels (see FIG. 3). The TOI module 110 generally selects bitplanes that are most reflective of the hemoglobin concentration changes and discards those that are not based on the color signature differences of hemoglobin and melanin (as described herein). In some cases, cardiovascular data from a physiological measurement system, such as an ECG, can be used as ground truth data for selection of the bitplanes. In this case, given that the facial vasculature is generally an integral part of the cardiovascular system, the hemodynamic changes in the face can correspond closely to the cardiovascular activities obtained from the physiological measurement system.

Figure 6:
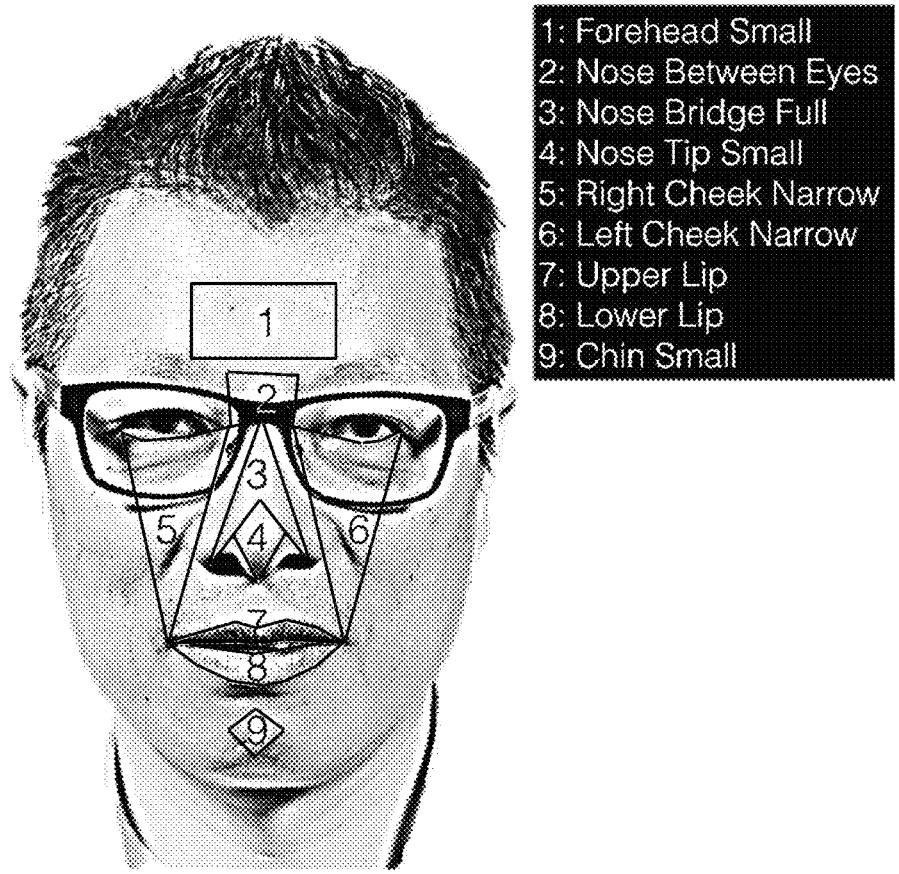
FIG. 6 is an exemplary illustration of an individual's face divided into regions of interest.

At block 204, in order to select the bitplanes, the TOI module 110 reduces dimensionality to defined regions of interest (ROIs). ROIs can be defined based on how blood flows and diffuses in the face or another part of the human skin surface, or according to other human anatomical features. For example, for the face, the TOI module can define nine ROIs: Forehead Small, Nose Between Eyes, Nose Bridge Full, Nose Tip Small, Right Cheek Narrow, Left Cheek Narrow, Upper Lip, Lower Lip, Chin Small. An example of these ROIs is illustrated in FIG. 6. For each ROI, the TOI module 110 obtains a raw temporal signal for the specific bitplane by averaging image values on each bitplane of each channel to reduce dimensionality. In this approach, the TOI module 110 defines region of interests on the image. For each bitplane, the TOI module 110 sums the bit values of all pixels in each region and divides the sum by the number of pixels in that region. This gives the average bit value for each ROI in each bitplane. Machine learning techniques, as described herein, can then be applied to obtain the best weights for all the ROIs in all the bitplanes, such that the system 100 can optimally predict the individual's stress level.

In some cases, the HC data from each ROI are treated as an independent signal. Thus, the HC data for each ROI is routed through a separate, individual corresponding signal processing path (also known as chain) which handles the specific TOI signal originating from a unique location on the facial image. In this way, multiple ROIs are generating multiple signals which are independently yet concurrently processed.

At block 206, the filtering module 112 band pass filters the raw signals in the pulse band (approximately 0.5 Hz to 2.5 Hz) from each channel. The present inventors have determined that if a particular bitplane contains information about systemic cardiovascular activity, such information can manifest itself in this band.

At block 208, the data science module 114 trains a machine learning model using the band pass filtered raw data from the RGB channels as the input and the ground truth pulse data from the physiological system as the target. A matrix of bitplane composition weights for an individual is obtained.

At block 210, the bitplane module 116 uses each individual's matrix of bitplane composition weights to select bitplanes from each frame of the individual's video images. In some cases, the TOI module 110 and/or the bitplane module 116 can track the individual's face in each frame and define the ROIs automatically.

At block 212, with the bitplanes selected, the TOI module 110 obtains the individual's raw facial blood flow signals from each ROI from the camera 105.

At block 214, in some cases, the transformation module 118 applies transformations to the filtered ROI signal to provide a principle frequency component of the TOI signal. This component can correspond to a periodic heart band frequency. In a particular case, the transformation can comprise using fast Fourier transform (FFT) and band pass filtering around the heart rate band (for example, 0.5 Hz to 2 Hz).

At block 216, using the principle frequency component, the reconstruction module 120 can reconstruct peaks of the individual's heartbeat to determine heart rate and determine intervals between heartbeats (i.e., RRI).

Having determined the peaks of heartbeat and determined RRIs, the stress module 122 determines a stress level for the individual based on approaches using the frequency domain, or the time domain, or using dynamic systems approaches. In an example, at block 218, the stress module 122 plots the RRIs, for example on a Poincaré plot for indexing heart rate variability (HRV). In a particular case, the stress module 122 plots each RRI against the next RRI on the plot; with RR(n) on the x-axis vs. RR(n+1) on the y-axis.

At block 220, the stress module 122 determines a second standard deviation of points along a line of identity to obtain "SD2." At block 222, the stress module 122 determines a first standard deviation of points perpendicular to the line of identity to obtain "SD1." In an example, the line of identity can be obtained using regression analysis or other suitable approach. At block 224, the stress module 122 determines an indicator of stress by dividing SD2 by SD1.

At block 226, the output module 124 outputs the stress determination to an output device 102; for example, to a computer monitor, a touchscreen, an LCD screen on a wearable device, an audible device, or the like.

The present inventors determined, through scientific testing, that TOI can non-invasively and accurately measure individual stress levels. As an example of such testing, individuals were presented short films, a neutral film for their resting period and a film to elicit a high-arousal emotion. Each individual's skin surface (in this case, their face) was recorded while they viewed the films. Transdermal facial blood flow data was extracted from pixels of each frame of the videos capturing the individuals' faces, as described herein. As a control, ECG was also attached to the individuals as they watched the films to compare the data.

In an example of such testing, seventy-nine healthy adults above 18 years of age (34 males; Mean Age=23.704 SD: 7.367) participated. Of the 79 participants, 19 participants completed the study twice and 20 participants completed the study thrice. Participants were told that they would be presented with a relaxing film; the film being an animated depiction of clouds moving through the sky for two minutes.

In this example, ECG data was acquired using a BIOPAC™ physiological measurement system with an electrocardiogram amplifier module (ECG100C) connected at a 250-Hz sampling rate. Electrodes were placed on participants based on Einthoven's triangle: near the right shoulder, left shoulder, and right hip. In this example, TOI image sequences were captured using a CCD camera angled to record the participants' face at 60 frames/seconds.

In this example, the accuracy of the TOI approach of the embodiments described herein was compared with measurements obtained with the BIOPAC ECG. Correlation coefficients of TOI and BIOPAC measurements were determined, specifically for measures of heart rate and standard deviation 2 (SD2) divided by standard deviation 1 (SD1); i.e., mental stress. These stress scores were transformed into a stress index. In this case, Fisher z-transformation was used to transform the correlation coefficients into z-values. A z-value is a standard score that represents the number of standard deviations the raw score is apart from the population mean. This allows an examination of the data on a normal distribution curve and allows for a determination of where an individual's stress score falls on a stress index. For example, the stress index can assume a mean of zero and a standard deviation of 1. A stress index of zero indicates average stress level, a stress index of 1 indicates a person's stress level is 1 standard deviation above the average, and a stress of −2 indicates a person's stress level is 2 standard deviations below the average. After obtaining stress indexes based on TOI and/or BIOPAC ECG, correlation coefficients of stress indexes were calculated to determine the correspondence between standard scores of heart rate and SD2/SD1 as obtained by TOI and the BIOPAC ECG.

Figure 7A:
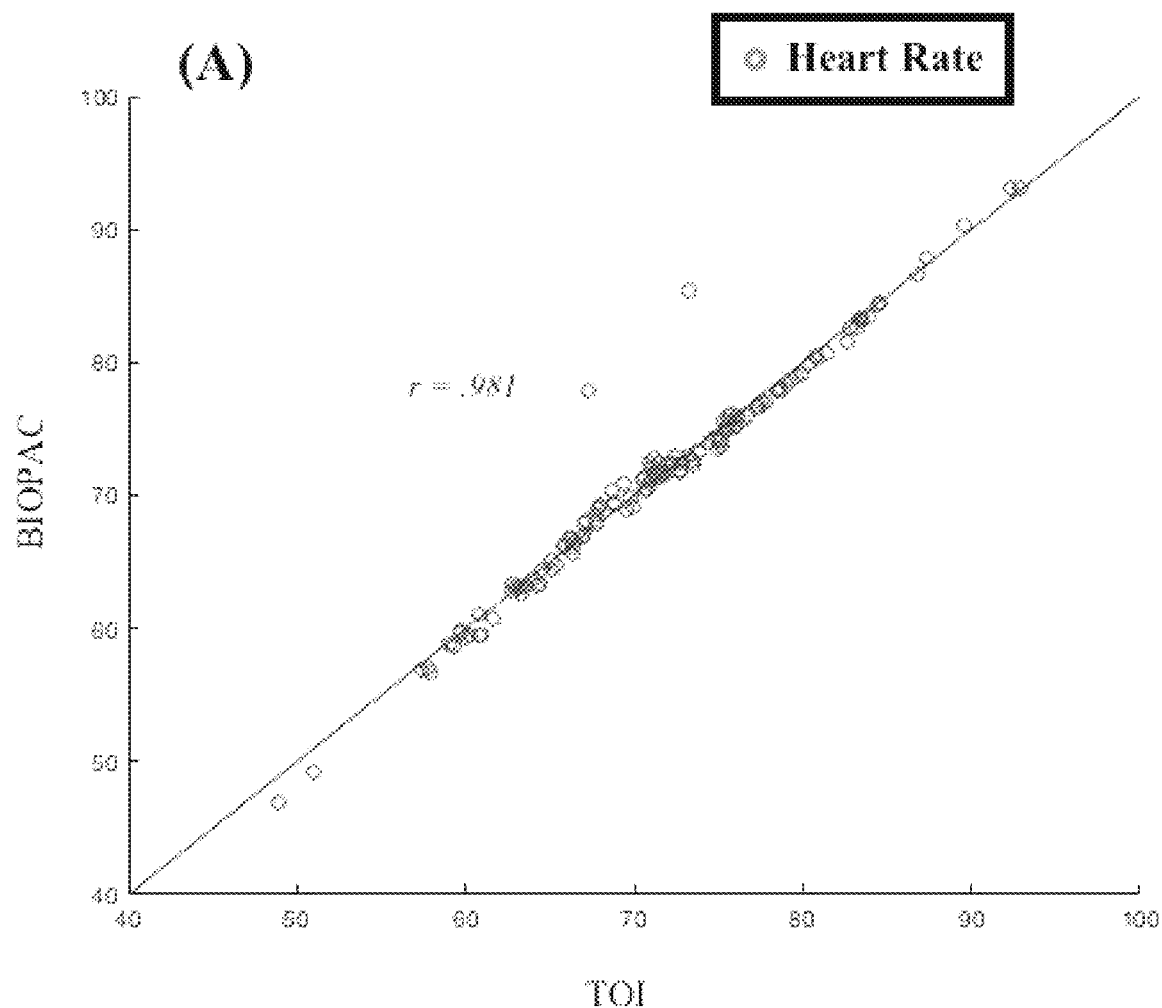
FIG. 7A is an exemplary chart comparing measurements of heart rate between the embodiment of FIG. 1 and electrocardiography.

A correlational analysis was conducted to examine the relationship between physiological measurements obtained from the embodiments described herein, using TOI, and those obtained with the BIOPAC ECG. A correlation between heart rate measurements obtained from TOI and BIOPAC was determined. It was found that there was a positive correlation between the two instruments, r=0.981. This extremely strong, positive correlation between measurements of heart rate obtained from TOI and those obtained from the BIOPAC ECG seem to indicate that TOI was able to detect heart rate approximately as accurately as the BIOPAC ECG (see FIG. 7A). The correlation between mental stress measurements obtained from TOI and BIOPAC was also determined. SD1 and SD2 was obtained from both instruments.

SD1 can be defined as the dispersion (standard deviation) between points in the direction perpendicular to the line of identity on the Poincare plot. SD1 reflects the short-term variation of heart rate caused by RSA, thus it can indicate the activation of the sympathetic nervous system. SD1 measurements can be obtained using the following formula:

$$SD1 = \frac{\sqrt{2}}{2} SD(RR_n - RR_{n+1})$$

SD2 can be defined as the dispersion (standard deviation) between points along the line of identity on the Poincare plot. SD2 reflects the long-term variation of heart rate caused by RSA, thus it can indicate the activities of the sympathetic and parasympathetic nervous system. SD2 measurements were obtained using the following formula:

$$SD2 = \sqrt{2SD(RR_n)^2 - \frac{1}{2}SD(RR_n - RR_{n-1})^2}$$

Figure 7B:
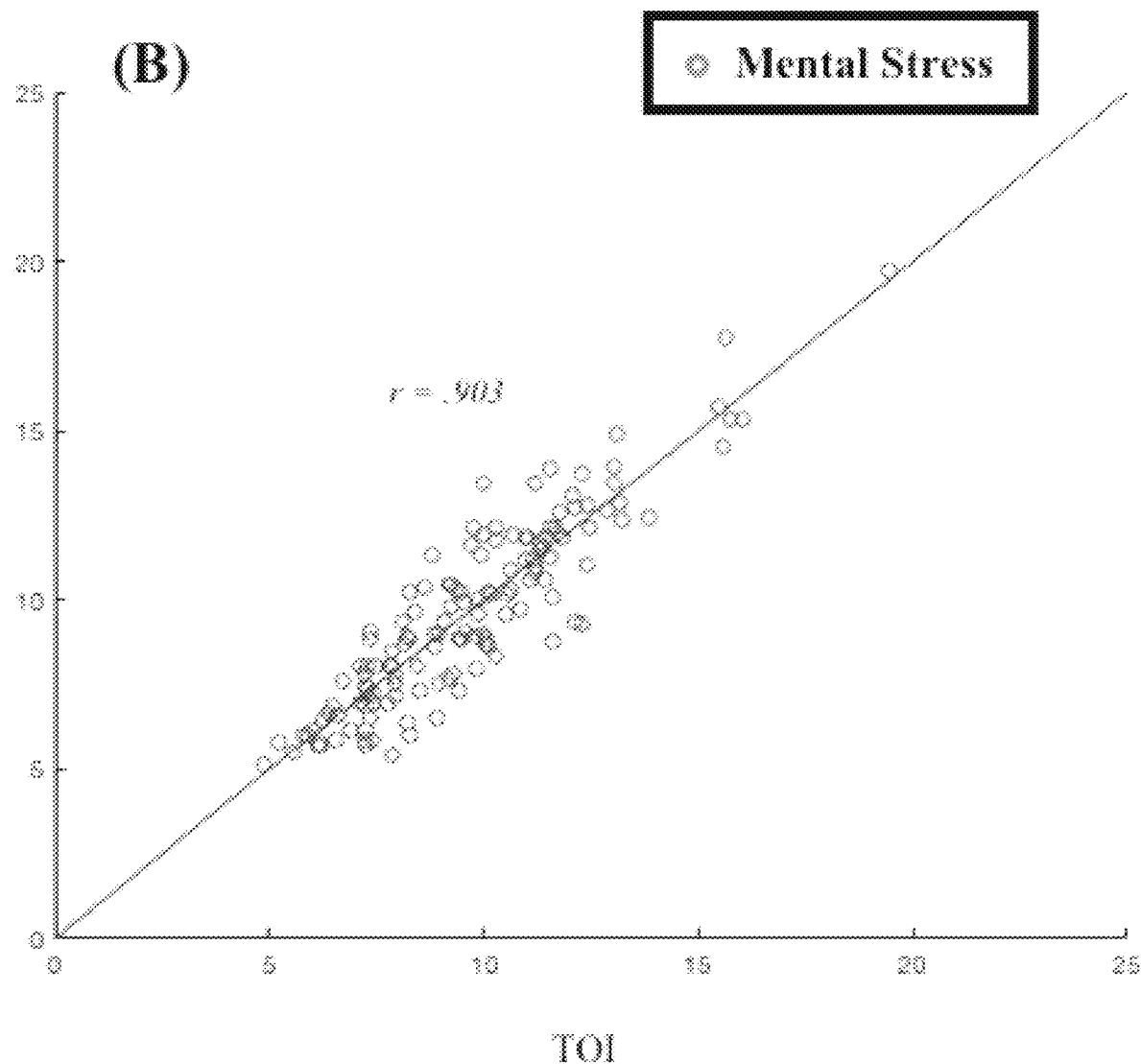
FIG. 7B is an exemplary chart comparing measurements of stress level between the embodiment of FIG. 1 and electrocardiography.

SD2/SD1 was determined as the ratio of dynamic change in the heart rate variability time series. SD2/SD1 reflects the relationship between the sympathetic and parasympathetic nervous system, which can be used as an indicator of individual stress. It was found that there was a positive correlation between the measurements of mental stress obtained from TOI and BIOPAC, r=0.903. This strong, positive correlation between measurements of mental stress obtained from TOI and BIOPAC seems to indicate that the TOI was able to determine mental stress approximately as accurately as the BIOPAC (see FIG. 7B). Thus, there were strong, positive correlations between physiological measurements obtained from TOI and those obtained from the BIOPAC ECG.

Advantageously, the embodiments described herein were found to provide a non-invasive approach to determine changes in human physiology, specifically heart rate and stress level, with at least the same amount of accuracy as other invasive and expensive approaches. Measurements of SD2/SD1 using the embodiments described herein corresponded strongly with those from the BIOPAC approach signifying that the present approach is able determine stress at least as accurately as the BIOPAC approach.

The present embodiments can advantageously be used, for example, to save a lot of cost, inconvenience, and expense currently used to determine heart rate variability (HRV) and stress by other approaches, such as with an ECG. ECG, in particular, is invasive in that it requires preparation of the patient's skin and involves the attachment of electrodes, which can be uncomfortable for some individuals. It can also be difficult to attach ECG electrodes onto certain individuals with a tendency to sweat excessively (e.g., those with diaphoresis) and at extremely humid locations; causing spontaneous detachment of electrodes from the individual, resulting in noisy and likely inaccurate ECG data. ECG equipment is also very expensive such that it is not commonly included in regular health examinations around the world, meaning that many people do not have easy access to procedures that inform them of their cardiovascular health or stress level.

The present embodiments advantageously provide an approach that is non-invasive, not susceptible to individual sweatiness, and relatively inexpensive. The present embodiments are non-invasive in that they require neither the preparation of the patient's skin nor the attachment of anything to the patient's body. This can minimize the amount of time medical staff spends to prepare patients for their physiological assessments to be conducted. In addition, fewer people are likely to have reservations regarding examinations of their cardiovascular health. Since the present embodiments do not require the attachment of electrodes onto the human body, they also do not require the individual to be assessed under specific conditions (for example, devoid of any skin condition and in a non-humid environment). Thus, more people can have the opportunity to measure their stress level. The present embodiments also generally require less expensive equipment to operate, and can be readily implemented in various settings. Thus, allowing stress to be monitored on a regular basis.

In various embodiments, the camera can be directed to the skin of any body part or parts, such as for example the hand, the abdomen, the feet, or the like. In these cases, the ROIs can be determined based on the structure of such body part. From these body areas, the system may also extract dynamic hemoglobin changes to determine stress level as described herein.

The foregoing embodiments may be applied to a plurality of fields. In one embodiment, the system may be installed in a smartphone device to allow a user of the smartphone to measure their stress level. In another embodiment, the system can be used in police stations and border stations to monitor the stress levels of suspects during interrogation. In yet further embodiments, the system can be used in medical or psychiatrist clinics for practitioners to monitor patients.

Other applications may become apparent.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A method for camera-based stress determination of a human individual, the method comprising:
   receiving an image sequence capturing a body part of the human individual;
   determining a plurality of regions-of-interest (ROIs) of the body part based on features of the body part;
   determining a set of bitplanes in the captured image sequence for each ROI that represent HC changes of the human individual using a trained machine learning model, the machine learning model trained with a hemoglobin concentration (HC) changes training set, the HC changes training set trained using bitplanes from previously captured image sequences of other human individuals as input and received cardiovascular data as targets;
   determining an HC change signal for each of the ROIs based on changes in the set of determined bitplanes;
   for each ROI, determining intervals between heartbeats based on peaks in the HC change signal;
   determining heart rate variability using the intervals between heartbeats;
   determining a stress level using at least one determination of a standard deviation of the heart rate variability; and
   outputting the stress level.

2. The method of claim 1, wherein the cardiovascular data comprises hemodynamic changes measured by an electrocardiograph.

3. The method of claim 1, wherein the bitplanes are in a red channel, green channel, and blue channel of each image of the image sequence.

4. The method of claim 1, wherein the machine learning model comprises a Long Short Term Memory (LSTM) neural network.

5. The method of claim 4, wherein the output of the LSTM neural network comprises a matrix of bitplane composition weights as the determined set of bitplanes.

6. The method of claim 1, wherein the body part is the individual's face.

7. The method of claim 6, wherein determining a plurality of ROIs comprises tracking the human individual's face in each frame of the captured image sequence to track the ROIs.

8. The method of claim 1, wherein determining intervals between heartbeats comprises:
   applying fast Fourier transform (FFT) and band pass filtering to determine a principle frequency component;
   using the principle frequency component, reconstructing peaks of each heartbeat; and
   determining intervals between the reconstructed peaks.

9. The method of claim 1, wherein determining heart rate variability comprises generating a Poincaré plot of the heartbeat intervals.

10. The method of claim 9, wherein determining the stress level comprises:
    determining a first standard deviation of points of heart rate variability in a direction perpendicular to a line of identity of the Poincare plot;
    determining a first standard deviation of points of heart rate variability in a direction that is along the line of identity;
    determining a measure of stress as a correlation to the second standard divided by the first standard deviation.

11. The method of claim 10, wherein determining the measure of stress further comprises performing a Fisher z-transformation to the second standard divided by the first standard deviation.

12. A system for camera-based stress determination of a human individual, the system comprising at least one processing unit and a data storage, the at least one processing unit in communication with the data storage and configured to execute:
    a transdermal optical imaging (TOI) module to receive an image sequence capturing a body part of the human individual, and to determine a plurality of regions-of-interest (ROIs) of the body part based on features of the body part;
    a data science module to determine a set of bitplanes in the captured image sequence for each ROI that represent HC changes of the human individual using a trained machine learning model, the machine learning model trained with a hemoglobin concentration (HC) changes training set, the HC changes training set comprising bitplanes from previously captured image sequences of other human individuals as input and received cardiovascular data as targets, the TOI module determining an HC change signal for each of the ROIs based on changes in the set of determined bitplanes;

a reconstruction module to determine intervals between heartbeats based on peaks in the HC change signal;

a stress module to determine heart rate variability using the intervals between heartbeats, and to determine a stress level using at least one determination of a standard deviation of the heart rate variability; and an output module to output the stress level.

13. The system of claim 12, wherein the cardiovascular data comprises hemodynamic changes received from an electrocardiograph.

14. The system of claim 12, wherein the bitplanes are in a red channel, green channel, and blue channel of each image of the image sequence.

15. The system of claim 12, wherein the body part is the individual's face.

16. The system of claim 15, wherein determining a plurality of ROIs comprises tracking the human individual's face in each frame of the captured image sequence to track the ROIs.

17. The system of claim 12, wherein the reconstruction module determines intervals between heartbeats by:

applying fast Fourier transform (FFT) and band pass filtering to determine a principle frequency component;

using the principle frequency component, reconstructing peaks of each heartbeat; and determining intervals between the reconstructed peaks.

18. The system of claim 12, wherein the stress module determines heart rate variability by generating a Poincare plot of the heartbeat intervals.

19. The system of claim 18, wherein the stress module determines the stress level by:

determining a first standard deviation of points of heart rate variability in a direction perpendicular to a line of identity of the Poincare plot;

determining a first standard deviation of points of heart rate variability in a direction that is along the line of identity;

determining a measure of stress as a correlation to the second standard divided by the first standard deviation.

20. The system of claim 19, the stress module determines the measure of stress by performing a Fisher z-transformation to the second standard divided by the first standard deviation.

* * * * *